United States Patent [19]

Hollingsworth et al.

[11] Patent Number: 5,214,155
[45] Date of Patent: May 25, 1993

[54] METHOD FOR 1,2-SUBSTITUTED IMIDAZOLINE COMPOSITIONS

[75] Inventors: Donald R. Hollingsworth, Austin; Jeffrey H. Edwards, Spring, both of Tex.

[73] Assignee: Texaco Chemical Company, White Plains, N.Y.

[21] Appl. No.: 875,464

[22] Filed: Apr. 29, 1992

[51] Int. Cl.$^5$ .............................................. C07D 31/415
[52] U.S. Cl. .................... 548/348.1; 548/347.1
[58] Field of Search ............. 548/347, 352, 347.1, 548/348.1

[56] References Cited

U.S. PATENT DOCUMENTS

| | | | |
|---|---|---|---|
| 2,878,234 | 3/1959 | Peterson | 528/117 |
| 4,324,917 | 4/1982 | McConnell | 564/479 |
| 4,578,518 | 3/1986 | Vanderpool et al. | 564/479 |
| 4,578,519 | 3/1986 | Larken et al. | 564/479 |
| 4,588,842 | 5/1986 | Vanderpool | 564/479 |
| 4,709,045 | 11/1987 | Kubo et al. | 548/352 |
| 4,855,440 | 8/1989 | Shumway et al. | 548/353 |

*Primary Examiner*—Mary C. Lee
*Assistant Examiner*—Lenora A. Miltenberger
*Attorney, Agent, or Firm*—James L. Bailey; Kenneth R. Priem; Richard A. Morgan

[57] ABSTRACT

This invention is a method for making 1,2-substituted imidazoline compositions utilizing a polyamine mixture containing a high concentration of linear polyamine. The polyamine is either triethylenetetramine or tetraethylenepentamine. The polyamine mixture is reacted with a fatty acid, fatty dimer acid or the fatty esters thereof to yield the 1,2-substituted imidazoline composition. The highly linear polyamine provides higher yields of the imidazoline compound in the composition.

4 Claims, No Drawings

METHOD FOR 1,2-SUBSTITUTED IMIDAZOLINE COMPOSITIONS

BACKGROUND OF THE INVENTION

1. Field of the Invention

The invention is a method of producing 1,2-substituted imidazoline compositions.

2. Related Publications in the Art

Compounds containing an imidazoline ring structure substituted at the number 1 and number 2 position are well-known in the art. Imidazolines substituted at the 2 position with a long chain aliphatic group are cationic compounds exhibiting surface active properties. They have been used as cationic emulsifiers, flotation agents, corrosion inhibitors and the like.

U.S. Pat. No. 4,709,045 to M. Kubo et al. discloses a process for producing 1,2-substituted imidazoline compounds. These compounds are formed from the reaction of dialkylenetriamine with a higher fatty acid.

U.S. Pat. No. 2,878,234 to L. E. Peterson discloses diimidazoline compounds. These are formed by the reaction of a polyamine such as triethylenetetramine or tetraethylenepentamine with an aliphatic dibasic acid.

U.S. Pat. No. 4,855,440 to D. F. Schumway et al. discloses stabilized imidazoline derivatives. The patent teaches that the numbering system for the imidazoline ring is conventional.

SUMMARY OF THE INVENTION

The invention is a method for producing a 1,2-substituted imidazoline composition. A polyamine mixture is reacted with a selected acidic compound at imidazoline reaction temperature and pressure. The polyamine mixture is selected from oligomers of triethylenetetramine and oligomers of tetraethylenepentamine. The acidic compound is selected from the group consisting of $C_8$ to $C_{30}$ fatty acids, esters thereof, dimer fatty acids thereof, dimer fatty esters thereof and mixtures thereof. The method is characterized in the polyamine mixture comprising 75 wt % or more linear triethylenetetramine oligomer or 65 wt % or more linear tetraethylenepentamine oligomer. As a result compositions, concentrated in 1,2-substituted imidazoline are recovered from polyamine feedstocks. These compositions are suitable for curing epoxy resins without additional separation or concentration.

DETAILED DESCRIPTION OF THE PREFERRED EMBODIMENTS

The polyamine mixture of the invention comprises linear triethylenetetramine or linear tetraethylenepentamine. These compounds are synthesized from the reaction of ethylenediamine and monoethanolamine in mole ratios of 1 to 5 moles of ethylenediamine per mole of monoethanolamine at catalytic reaction temperature and pressure. The catalyst used is generally a thermally activated, calcined pelleted titania having active phosphorus sites chemically bonded to the surface. The reaction is carried out in a continuous process of about 250° C. to 400° C. and pressure of 500 to 3000 psig sufficient to maintain the reaction mixture in the liquid phase.

The preparation of these compounds is well documented in the patent literature. For example, U.S. Pat. No. 4,324,917 to T. T. McConnell incorporated herein by reference teaches that a commercially available cation exchange resin was used to convert a 2/1 mole ratio mixture of ethylenediamine and monoethanolamine at a temperature of 305° C. and a pressure of 1500 psig and liquid hourly space velocity of 1 gm/hr ml catalyst volume to linear products. The noncyclic content of the triethylenetetramine compounds was 96.8%.

For the purpose of clarity in interpreting the claims appended hereto we define the terms triethylenetetramine and linear triethylenetetramine as follows. The catalytic reaction of ethylenediamine with monoethanolamine yields a product mixture comprising unreacted ethylenediamine and monoethanolamine along with a number of linear, branched and cyclic reaction products. The product mixture is fractionally distilled to recover an unreacted fraction which is recycled to the process. Another fraction contains triethylenetetramine.

Triethylenetetramine is the generic term for four compounds:
linear triethylenetetramine,
nitrilotrisethylamine,
diaminoethylpiperazine, and
piperazinoethylethylenediamine.

By definition, triethylenetetramine refers to the mixture of four compounds. Linear triethylenetetramine refers only to the linear product having the structural formula:

Nitrilotrisethylamine has a branched structural formula:

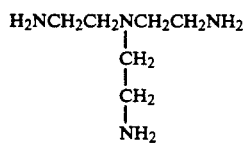

Diaminoethylpiperazine has the cyclic structural formula:

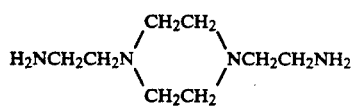

Piperazinoethylethylenediamine has the cyclic structural formula:

Correspondingly, tetraethylenepentamine is the generic term for four compounds:
linear tetraethylenepentamine,
aminoethyltriethylenetetramine,
aminoethylpiperazinylethylethylenediamine, and
piperazinylethyldiethylenetriamine.

By definition, tetraethylenepentamine refers to the mixture of four compounds. Linear tetraethylenepentamine refers only to the linear product having the structural formula:

Aminoethyltriethylenetetramine has a branched structural formula:

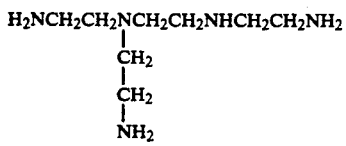

Aminoethylpiperazinylethylethylenediamine has the cyclic structural formula:

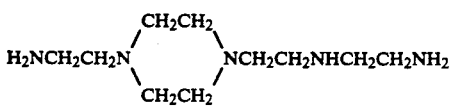

Piperazinylethyldiethylenetriamine has the cyclic structural formula:

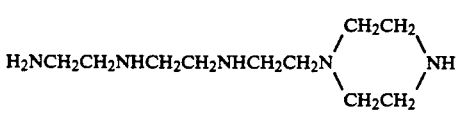

The linear oligomers have the greatest commercial value. For that reason, the patent art contains a number of catalysts which are useful in improving the yield of the linear oligomers. These include U.S. Pat. No. 4,588,842 to S. H. Vanderpool; U.S. Pat. No. 4,578,518 to S. H. Vanderpool et al. and U.S. Pat. No. 4,578,519 to J. M. Larkin et al. all incorporated herein by reference in their entirety. In general, these patents teach that by reaction and fractional distillation, a triethylenetetramine mixture is produced which contains at least about 75 wt % of the linear triethylenetetramine. Process optimization yields a product which contains at least 80 wt % of the linear product. The T. T. McConnell patent teaches that a product containing 96.8% of the noncyclic material has been made. Likewise, a tetraethylenepentamine mixture is produced containing at least 65 wt % of the linear oligomer. Process optimization yields a product containing 70 wt % linear oligomer. These high concentration linear oligomer mixtures are the feedstocks for 1,2-substituted imidazoline.

Fatty acids are typically monobasic aliphatic, unsaturated polyunsaturated acids containing from about 8 to 30 carbon atoms and often from about 12 to 22 carbon atoms. Fatty acids are derived from vegetable fat or oil, though they can be recovered from fish or animal fat or oil or can be entirely synthetic. Fatty acids derived from natural sources are usually a mixture of acids. For example tall oil fatty acid is a mixture consisting primarily of oleic acid and linoleic acid. Tall oil fatty acid is a by-product of digesting pinewood in the kraft paper process.

Representative fatty acids include: caproic, heptanoic, caprylic, decenoic, undecanoic, lauric, dodecanoic, tridecanoic, myristic, tetradecenoic, pentadecenoic, hexadecanoic, palmitic, heptadecenoic, stearic, oleic, nonadecanoic, eicosanoic, behenic, tetracosanoic and the like. Fatty acid mixtures include fatty acids derived from tallow, soybean and coconut oil.

Included in the invention are also esters, particularly alkyl esters, of these fatty acids, referred to as fatty esters. This includes the esterification product with organic alcohols such as methanol, ethanol and propanol. The methyl ester is preferred.

Fatty acids which are unsaturated can be condensed to form dimer fatty acids. Examples of these dimer fatty acids include adipic, sebacic, azelaic, glutaric, succinic, oxalic, malonic, maleic, etc. These dimer fatty acids contain two carboxylic acid groups, both of which can react with polyamine to form diimidazolines. These diimidazolines are disclosed, for example, in U.S. Pat. No. 2,878,234 to L. E. Peterson. The esters of these dimer fatty acids are also useful. Again the methyl ester and diester are preferred.

Imidazoline compositions are formed in a two step reaction. The relative amounts of reactants are such that the carboxylic acid or ester groups are present in excess over the stoichiometric amount required for reaction with the polyamine. Stoichiometry would dictate a carboxylic acid or ester:polyamine ratio of 1:1. In practice a ratio of 1.5:1 to 1.8:1 is used so that all of the polyamine is reacted.

The initial condensation of the fatty acid and polyamine may be carried out at a temperature of 120° C. to 200° C. under inert atmosphere. This is followed by the cyclization reaction carried out at a temperature of 195° C. to 290° C. carried out at reduced pressure of 1 to 50 mm Hg, preferably 10 to 30 mm Hg. The extent of cyclization can be followed by analyzing the imidazoline to amide ratio by infrared spectrocopy (IR). Heating is terminated when the imidazoline to amide ratio produces an optimum yield. Alternatively, heating may be terminated when sufficient time has passed for optimum yield to be achieved based on past experience. The maximum time required is generally 10 hours and typically 3 to 8 hours. The liquid reaction product is allowed to cool to room temperature and sampled for quality control.

It has been found that polyamine mixtures comprising these high concentrations of linear polyamine produce reaction products that do not require separation or other purification prior to use as epoxy resin curatives.

This invention is shown by way of Example.

EXAMPLE 1

To a 4-neck flask equipped with a mechanical stirrer, dean-stark trap and condenser, thermometer and argon inlet was added 125 g (0.66 mol) tetraethylenepentamine (TEPA) comprising 73.8% linear TEPA (TEXLIN ® 400). To this TEPA was added 375 g tall oil fatty acid (TOFA) (FA2 Acintol, 1.32 mol) and the mixture was heated to 190° C. for 3 hours. The material was then cooled and analyzed with the following results:

| | |
|---|---|
| % Imidazoline, by NMR | 15.6 |
| Total Amine, meq/g | 3.9 |
| Primary Amine, meq/g | 0.8 |
| Secondary Amine, meq/g | 2.6 |
| Tert. Amine, meq/g | 0.6 |
| water, Wt % | 0.4 |
| Color, Gardner | 7 |
| Viscosity @ 25° C., cps | 1481 |

EXAMPLE 2—COMPARATIVE

Example 1 was repeated with TEPA containing 51.5% linear TEPA. This imidazoline product was analyzed with the following results:

| | |
|---|---|
| % Imidazoline, by NMR | 8.3 |
| Total Amine, meq/g | 3.8 |
| Primary Amine, meq/g | 1.8 |
| Secondary Amine, meq/g | 1.1 |
| Tert. Amine, meq/g | 0.9 |
| water, Wt % | 0.5 |
| Color, Gardner | 8 |
| Viscosity @ 25° C., cps | 1672 |

EXAMPLE 3—COMPARATIVE

Example 1 was repeated with TEPA containing 48.5% linear TEPA. This imidaxoline product was analyzed with the following results:

| | |
|---|---|
| % Imidazoline, by NMR | 7.2 |
| Total Amine, meq/g | 3.8 |
| Primary Amine, meq/g | 0.5 |
| Secondary Amine, meq/g | 2.3 |
| Tert. Amine, meq/g | 1.0 |
| water, Wt % | 0.3 |
| Color, Gardner | 7 |
| Viscosity @ 25° C., cps | 1770 |

EXAMPLE 4

Example 1 was repeated at a reaction temperature of 210° C. This imidazoline product was analyzed with the following results:

| | |
|---|---|
| % Imidazoline, by NMR | 25.7 |
| Total Amine, meq/g | 4.0 |
| Primary Amine, meq/g | 0.5 |
| Secondary Amine, meq/g | 2.3 |
| Tert. Amine, meq/g | 1.0 |
| water, Wt % | 0.3 |
| Color, Gardner | 7 |
| Viscosity @ 25° C., cps | 1770 |

EXAMPLE 5—COMPARATIVE

Example 4 was repeated with TEPA containing 51.5% linear TEPA. This imidazoline product was analyzed with the following results:

| | |
|---|---|
| % Imidazoline, by NMR | 20.6 |
| Total Amine, meq/g | 3.8 |
| Primary Amine, meq/g | 0.6 |
| Secondary Amine, meq/g | 2.2 |
| Tert. Amine, meq/g | 1.1 |
| water, Wt % | 0.23 |
| Color, Gardner | 6 |
| Viscosity @ 25° C., cps | 2096 |

EXAMPLE 6—COMPARATIVE

Example 4 was repeated with TEPA containing 48.5% linear TEPA. This imidazoline product was analyzed with the following results:

| | |
|---|---|
| % Imidazoline, by NMR | 18.9 |
| Total Amine, meq/g | 3.9 |
| Primary Amine, meq/g | 0.6 |
| Secondary Amine, meq/g | 2.1 |
| Tert. Amine, meq/g | 1.1 |
| water, Wt % | 0.24 |
| Color, Gardner | 6 |
| Viscosity @ 25° C., cps | 1277 |

EXAMPLE 7

To a 4-neck flask equipped with a mechanical stirrer, condenser, thermometer an argon inlet was added 101.6 g (0.69 mol) of triethylenetetramine (TETA) containing 84.1% linear TETA (TEXLIN ® 300). To this TETA was added 161.5 g of $C_{16}$–$C_{60}$ dimer acid having an average molecular weight of $C_{38}$ (Unidyme 22, 0.28 mol). The mixture was heated to 165° C. for 2 hours. A vacuum of 75 mm of Hg was applied and the temperature was increased to 235° C. for 5 hours. The material was then cooled and analyzed with the following results:

| | |
|---|---|
| Imidazoline/Amide Ratio, by IR | 8.2 |
| Total Amine, meq/g | 8.5 |
| Tert. Amine, meq/g | 0.9 |
| Color, Gardner | 7 |
| Viscosity, @ 25° C., cps | 1202 |

EXAMPLE 8—COMPARATIVE

Example 7 was repeated with TETA containing 64.5% linear TETA. The imidazoline product was analyzed with the following results:

| | |
|---|---|
| Imidazoline/Amide Ratio, by IR | 5.9 |
| Total Amine, meq/g | 6.6 |
| Tert. Amine, meq/g | 1.6 |
| Color, Gardner | 10 |
| Viscosity @ 25° C., cps | 3198 |

EXAMPLE 9—COMPARATIVE

Example 7 was repeated with TETA containing 71.3% linear TETA. This imidazoline product was analyzed with the following results:

| | |
|---|---|
| Imidazoline/Amide Ratio by IR | 5.1 |
| Total Amine, meq/g | 7.8 |
| Tert. Amine, meq/g | 1.1 |
| Color, Gardner | 9 |
| Water, wt % | 0.14 |
| Viscosity @ 25° C., cps | 2083 |

EXAMPLE 10—COMPARATIVE

Example 7 was repeated with TETA containing 63.0% linear TETA. This imidazoline product was analyzed with the following results:

| | |
|---|---|
| Imidazoline/Amide Ratio, by IR | 3.0 |
| Total Amine, meq/g | 7.6 |
| Tert. Amine, meq/g | 1.3 |
| Color, Gardner | 7 |
| Water, wt % | 0.18 |

While particular embodiments of the invention have been described, it will be understood, of course, that the invention is not limited thereto since many modifications may be made, and it is, therefore, contemplated to cover by the appended claims any such modification as fall within the true spirit and scope of the invention.

What is claimed is:

1. A method for making a 1,2-substituted imidazoline composition comprising:

reacting a polyamine mixture comprising triethylenetetramine oligomers with an acidic compound selected from the group consisting of $C_8$ to $C_{30}$ fatty acids, esters thereof, dimer fatty acids thereof, fatty esters thereof and mixtures thereof at imidazoline reaction temperature and pressure, characterized in that:

said polyamine mixture comprises 75 wt % or more linear triethylenetetramine oligomer.

2. The method of claim 1 wherein the polyamine mixture comprises 80 wt % or more linear triethylenetetramine oligomer.

3. A method for making a 1,2-substituted imidazoline composition comprising:

reacting a polyamine mixture comprising tetraethylenepentamine oligomers with an acidic compound selected from the group consisting of $C_8$ to $C_{30}$ fatty acids, esters thereof, dimer fatty acids thereof, fatty esters thereof and mixtures thereof at imidazoline reaction temperature and pressure, characterized in that:

said polyamine mixture comprises 65 wt % or more linear tetraethylenepentamine oligomer.

4. The method of claim 1 wherein the polyamine mixture comprises 70 wt % or more linear tetraethylenepentamine oligomer.

* * * * *